US012685629B2

(12) United States Patent
Kucklick et al.

(10) Patent No.: US 12,685,629 B2
(45) Date of Patent: Jul. 21, 2026

(54) SYSTEM, DEVICE AND METHOD FOR REPAIRING A ROTATOR CUFF TEAR

(71) Applicant: KiriGenX, Inc., Phoenix, AZ (US)

(72) Inventors: Theodore R. Kucklick, Scotts Valley, CA (US); Louis McIntyre, Winston Salem, NC (US); Robert T. Burks, Salt Lake City, UT (US)

(73) Assignee: KiriGenX, Inc., Phoenix, AZ (US)

( * ) Notice: Subject to any disclaimer, the term of this patent is extended or adjusted under 35 U.S.C. 154(b) by 0 days.

(21) Appl. No.: 19/024,100

(22) Filed: Jan. 16, 2025

(65) Prior Publication Data

US 2025/0235306 A1        Jul. 24, 2025

Related U.S. Application Data

(60) Provisional application No. 63/624,601, filed on Jan. 24, 2024.

(51) Int. Cl.
*A61F 2/08* (2006.01)
*A61B 17/00* (2006.01)

(52) U.S. Cl.
CPC ...... *A61F 2/0811* (2013.01); *A61B 17/00234* (2013.01); *A61B 2017/00238* (2013.01)

(58) Field of Classification Search
CPC ..... A61B 17/00234; A61B 2017/00238; A61F 2/0063; A61F 2/08; A61F 2/0811
See application file for complete search history.

(56) References Cited

U.S. PATENT DOCUMENTS

| | | | |
|---|---|---|---|
| 8,894,713 B2 * | 11/2014 | Shohat | A61F 2/30756 |
| | | | 606/90 |
| 10,813,742 B2 * | 10/2020 | Adams | A61B 17/3423 |
| 11,369,486 B2 * | 6/2022 | Tennent | A61B 17/1778 |

* cited by examiner

*Primary Examiner* — Larry E Waggle, Jr.

(74) *Attorney, Agent, or Firm* — Crockett & Crockett, PC; K. David Crockett, Esq.; Niky Economy Syrengelas

(57) ABSTRACT

A delivery device used to deploy a biological construct into the glenohumeral joint space for minimal disruption to repair a partial rotator cuff tear. The biological construct is positioned on the articular side of the tendon tear and introduced into the joint space so that the construct supports the tear without further tearing or damaging the tendon. The patch is secured to the tear with stiches on the bursal side of the tear.

6 Claims, 7 Drawing Sheets

SYSTEM, DEVICE AND METHOD FOR REPAIRING A ROTATOR CUFF TEAR

This application claims priority to U.S. Provisional Application 63/624,601, filed Jan. 24, 2024.

FIELD OF THE INVENTIONS

The inventions described below relate to the field of systems and methods of arthroscopic repair of torn shoulder tendons.

BACKGROUND OF THE INVENTIONS

Rotator cuff tears are a prevalent condition, particularly among athletes and the aging population. It has been reported that many people over the age of 50 have a partial rotator cuff tear with 70% of those over 70 with a partial tear. This represents about 47 million people in the U.S. and 1.2 billion people worldwide. Only 30% of those tears are on the bursal side, and 70% are on the articular side. Without treatment, these partial tears can progress to full thickness tears.

Conventional surgery repair techniques include arthroscopic repair of the partial tendon by completion of the partial tear in order to access the articular side of the tear. While these methods have demonstrated success in restoring function, they present challenges in the healing process and a significant increase in morbidity rates.

There remains a need for more effective and less invasive methods that improve healing times and provide superior outcomes and better recovery, especially for partial tears on the previously inaccessible articular side of an intact rotator cuff. The devices and methods below optimize tendon repair, promote biological healing and minimize the risk of post operative complications resulting in improved functional recovery.

SUMMARY

The devices and methods described below provide for improved access with minimal disruption to repair a partial rotator cuff tear. A delivery device is used to deploy a regenerative biological construct or patch into the glenohumeral joint space. The construct is positioned on the articular side of the tendon tear and introduced into the joint space so that the construct supports the tear without further tearing or damaging the tendon. The construct is secured to the tear with stiches on the bursal side of the tear. A delivery cone is inserted into an anterior cannula for insertion of the biological construct or patch onto the articular or bottom side of the tendon tear. The biological construct has suture tails on an end of the construct. The construct is compressed to the articular side of the rotator cuff with the sutures and tensioned with the sutures on the bursal side of the tear without requiring a full or completed tear of the torn tendon. The sutures are then tied to the bursal side of the tear with the construct compressed to the articular side of the tear. Once the construct is delivered to the repair site, the suture is then pulled to the tear and tensioned against the construct to secure the construct against the articular side tear of the rotator cuff.

DETAILED DESCRIPTION OF THE INVENTIONS

Figure 1:
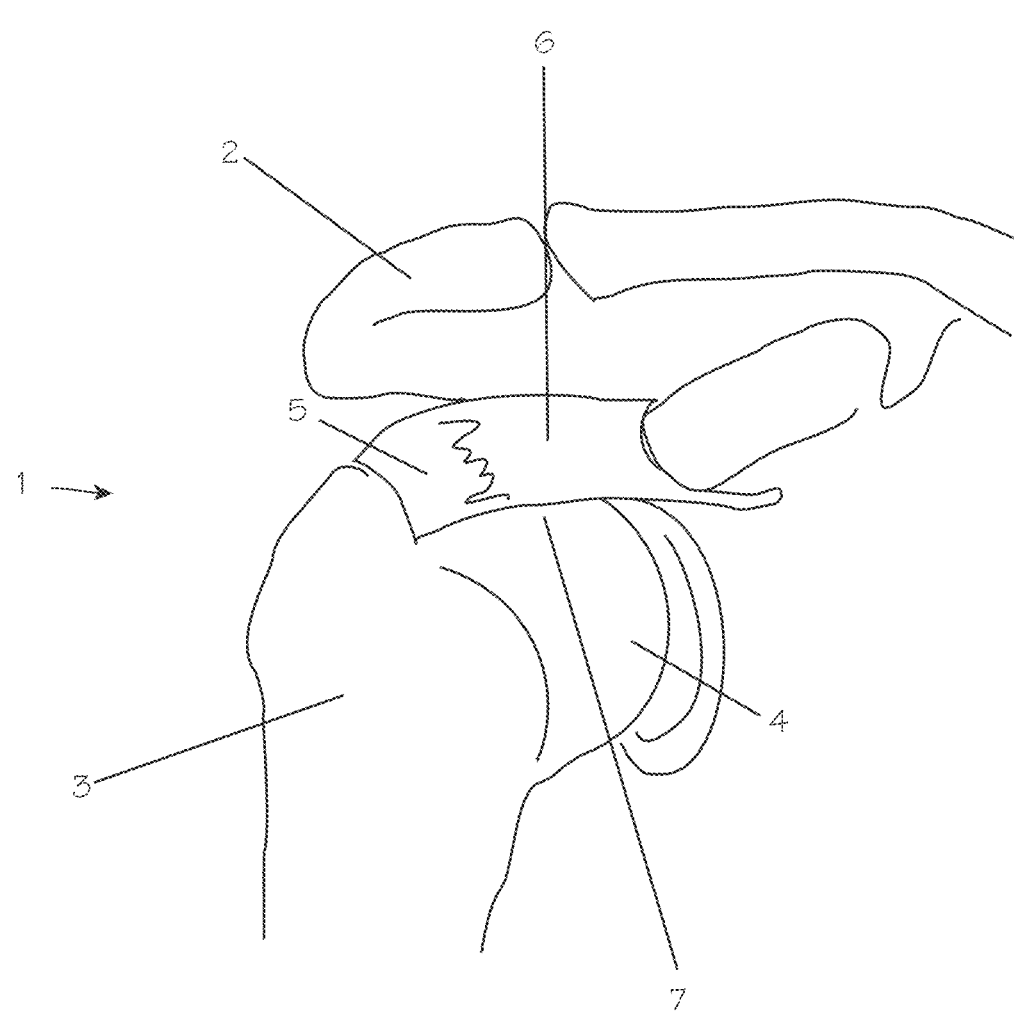
FIG. 1 illustrates the significant shoulder anatomy of a patient shoulder including the glenohumeral and subacromial space.

FIG. 1 illustrates the significant shoulder anatomy of a patient shoulder 1 including the glenohumeral and subacromial space. The figure illustrates the acromion 2, humerus 3 glenohumeral joint 4 and supraspinatus 5 of the shoulder. The figure shows a rotator cuff having a bursal or top side of the rotator cuff tear 6 and an articular or bottom side of the rotator cuff tear 7.

Figure 2:
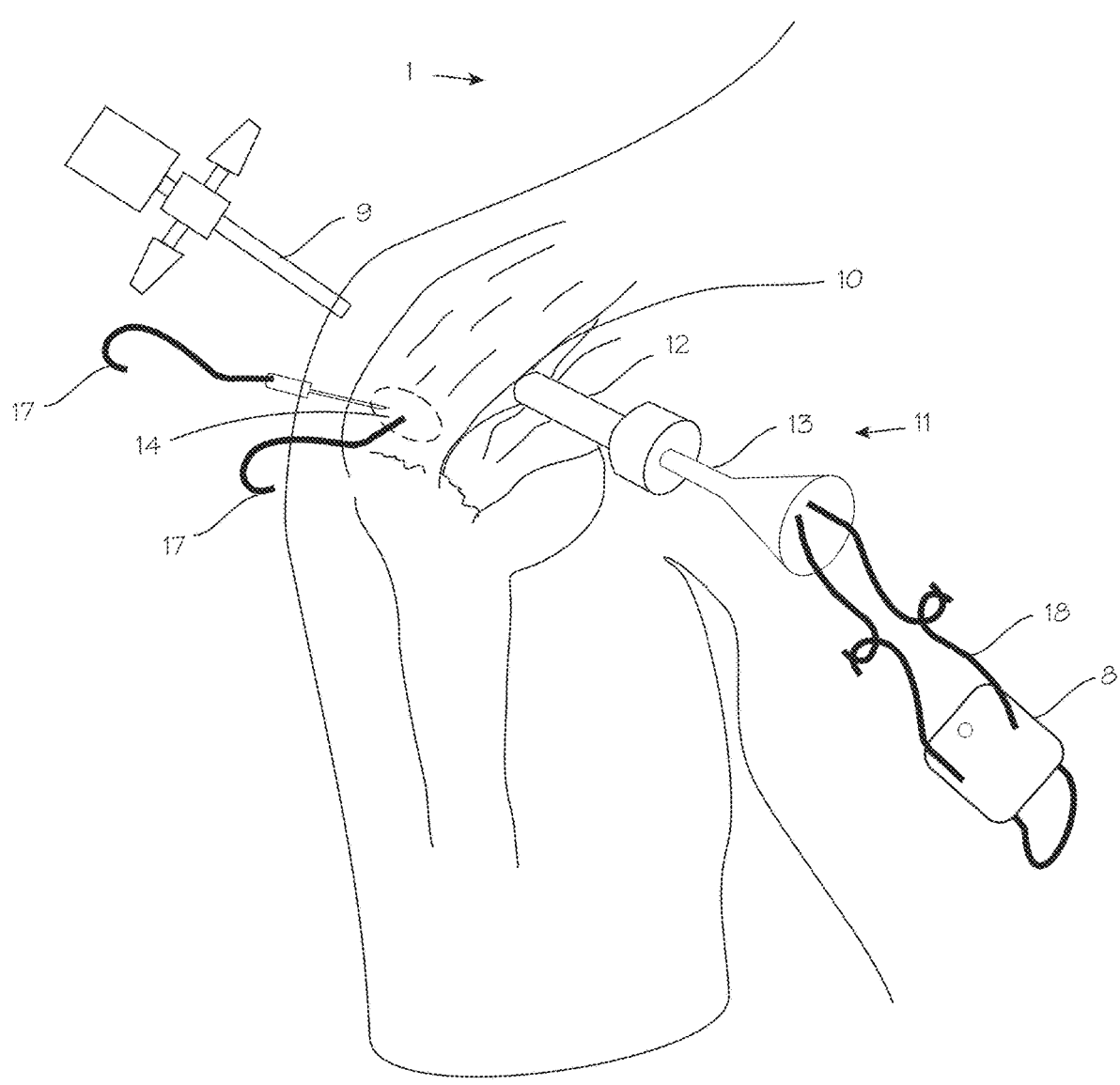
FIG. 2 illustrates the method for placement of a biological construct or patch installed on the articular side or bottom side of the tear of a shoulder tendon of a patient.

FIG. 2 illustrates the method for placement of a biological construct or patch 8 installed on the articular side or bottom side of a patient with a torn shoulder tendon. First, a viewing portal is established through a posterior portal of the shoulder. The viewing portal can be distended for introduction of a scope 9 for viewing. Then, a first surgical opening 10 is established in the shoulder to create an arthroscopic or anterior portal. The first surgical opening establishes the arthroscopic or anterior portal through the rotator cuff interval. The arthroscopic or anterior portal could be any anterior portal accessing the glenohumeral space. The arthroscopic or anterior portal can include a delivery device 11 inserted therethrough for insertion of sutures and tools. The delivery device can further include an anterior cannula 12 and roller cone 13. The anterior cannula is then inserted into the arthroscopic or anterior portal. A second surgical opening 14 is then established to create a lateral portal and introduce a lateral cannula 15 (shown in FIG. 3). The lateral portal can accommodate a grasper 16 (shown in FIG. 5). After the anterior cannula is inserted, two or more traction sutures 17 are pushed through a spinal needle from the lateral portal, passed through the rotator cuff and pulled out of the anterior cannula via the grasper (shown in FIG. 5). The traction sutures can be Polydioxanone (PDS) traction sutures. The traction sutures are then pulled out of the anterior portal cannula with the grasper. The PDS sutures serve to retract tissue to improve visibility and access during the procedure. The delivery roller cone 13 is inserted into the anterior cannula 12 for insertion of a biological construct or patch onto the articular or bottom side of the tendon tear 7. The biological construct has suture tails 18 on an end of the construct. The traction sutures 15 are tied to the suture tails 18 of the biological construct.

Figure 8:
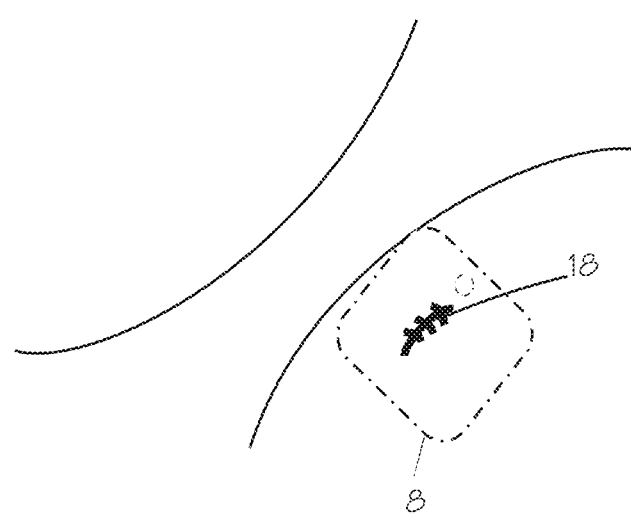
FIG. 8 illustrates the knotted sutures on the bursal side after placement of the construct against the articular side tear.

Outside the delivery device, the construct is in a first unrolled position, then inserted through the delivery device in a second rolled position (shown in FIG. 3), and then advanced through the delivery device and expanded back into an open or unrolled position. The construct is advanced through the delivery device and unrolled when positioned in the glenohumeral joint space of the shoulder. A driver or inserter 19 (shown in FIG. 3) may be used to push the biological construct to the glenohumeral joint space while the traction sutures are pulled on at the same time. The construct exits the distal end of the delivery device and is positioned on the articular side or bottom side of the tear. The construct is attached to a suture tail long enough to follow the construct to the tendon repair site at a first end and also trail to the top of the tendon surface at the second end. The biological construct is pulled against the articular sided tear with the traction sutures. The traction sutures pull the surgical sutures through the rotator cuff. The construct suture tails are then pulled out of the lateral cannula and clipped off. The sutures are then tied to the bursal side of the rotator cuff with the implant compressed to the articular side of the rotator cuff. Once the patch is delivered to the repair site, the suture is then pulled to the tear and tensioned against the compressed patch to secure the patch against the articular side tear of the rotator cuff. To tension the patch, the suture is pulled from the first end to oppose the patch to the tendon tear. The second suture end that is on the bursal or top side is also tightened or pulled and secured to the tendon or bone to ensure secure placement of the patch. A knot is tied in the surgical suture, pushed through the lateral cannula and the knot is tied down to the bursal surface while excess surgical suture is clipped off. FIG. 8 illustrates the suture ties on the bursal side of the tendon being optionally secured to a pledget, sponge, pack or plate or anything absorbent to help manage fluids and hold a bioactive substance. The pledget is applied to bursal side to provide a means to cinch the sutures.

Figure 3:
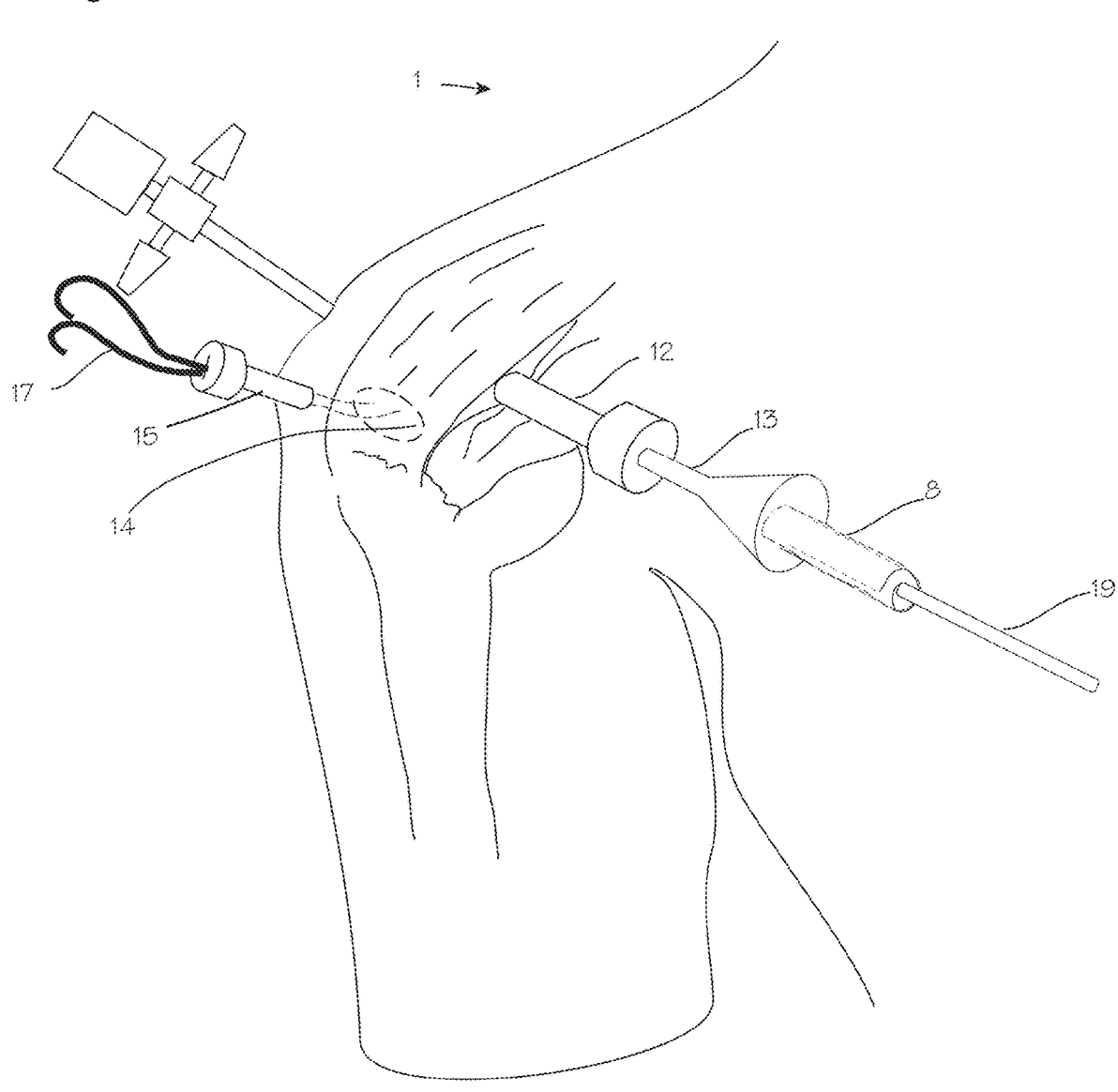
FIG. 3 illustrates the method for placement of a biological construct or patch installed on the articular side or bottom side of the tear of a shoulder tendon of a patient with a rolled construct loaded into a roller cone.

FIG. 3 illustrates the method for placement of a biological construct or patch installed on the articular side or bottom side of the tear of a shoulder tendon of a patient with a rolled construct loaded into the roller cone. The delivery cone 14 is inserted into the anterior portal 10 for insertion of the biological construct onto the articular or bottom side of the tendon tear. The figure illustrates the construct after the traction sutures have been tied to the construct suture tails have been tied to the suture ties and rolled from a first unrolled position to a second rolled position and loaded into the roller cone. The construct is then advanced through the delivery device and expanded back into an open or unrolled position. The construct is advanced through the delivery device and unrolled when positioned in the glenohumeral joint space of the shoulder. The driver 19 may be used to push the biological construct to the glenohumeral joint space. The construct exits the distal end of the delivery device and is positioned on the articular side or bottom side of the tear. Once the construct is delivered to the repair site, the suture is then pulled to the tear and tensioned against the compressed patch to secure the patch against the articular side tear of the rotator cuff.

Figure 4:
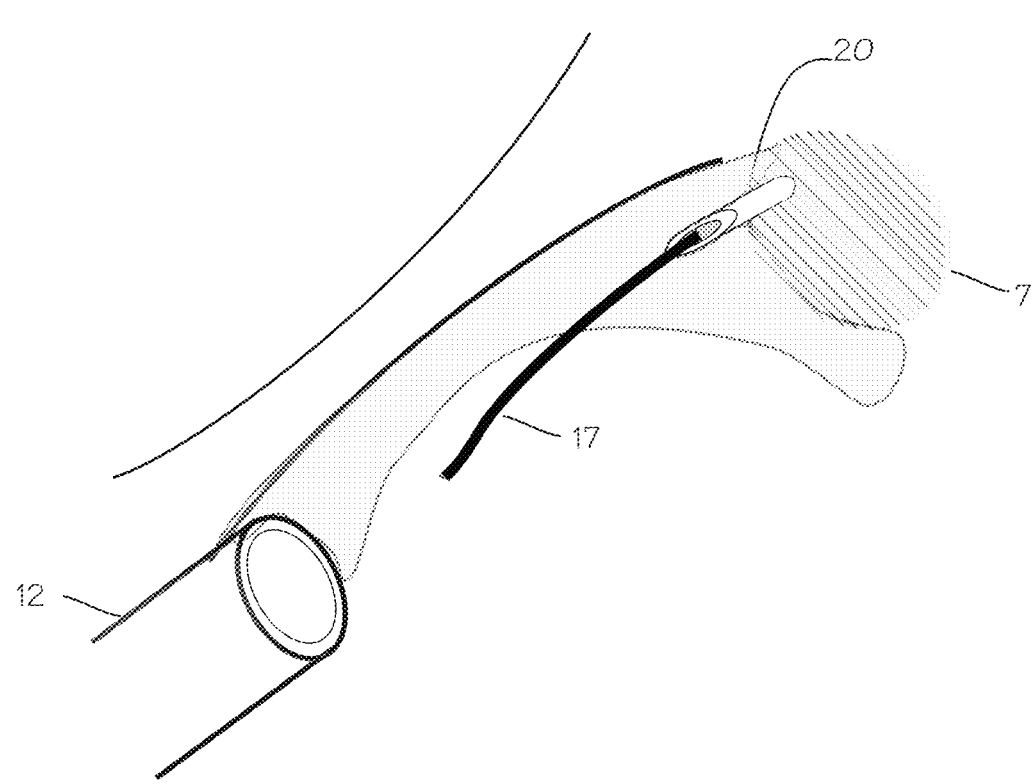
FIG. 4 illustrates the view of the glenohumeral space and the articular sided tear with the spinal needle and anterior cannula inserted.

FIGS. 4 through 8 illustrate path of the construct as it is positioned onto the articular sided tear. FIG. 4 illustrates the view of the glenohumeral space and the articular sided tear with the spinal needle and anterior cannula inserted through the articular sided tear. This figure illustrates the arthroscopic view 10 into the glenohumeral space, viewing the articular sided tear. Access to the space can be achieved by advancement of a spinal needle 20 through the articular sided tear 7. The traction sutures are passed into the glenohumeral space through rotator cuff through the spinal needle. The sutures can be retrieved through the cannula in the anterior portal through the rotator interval.

Figure 5:
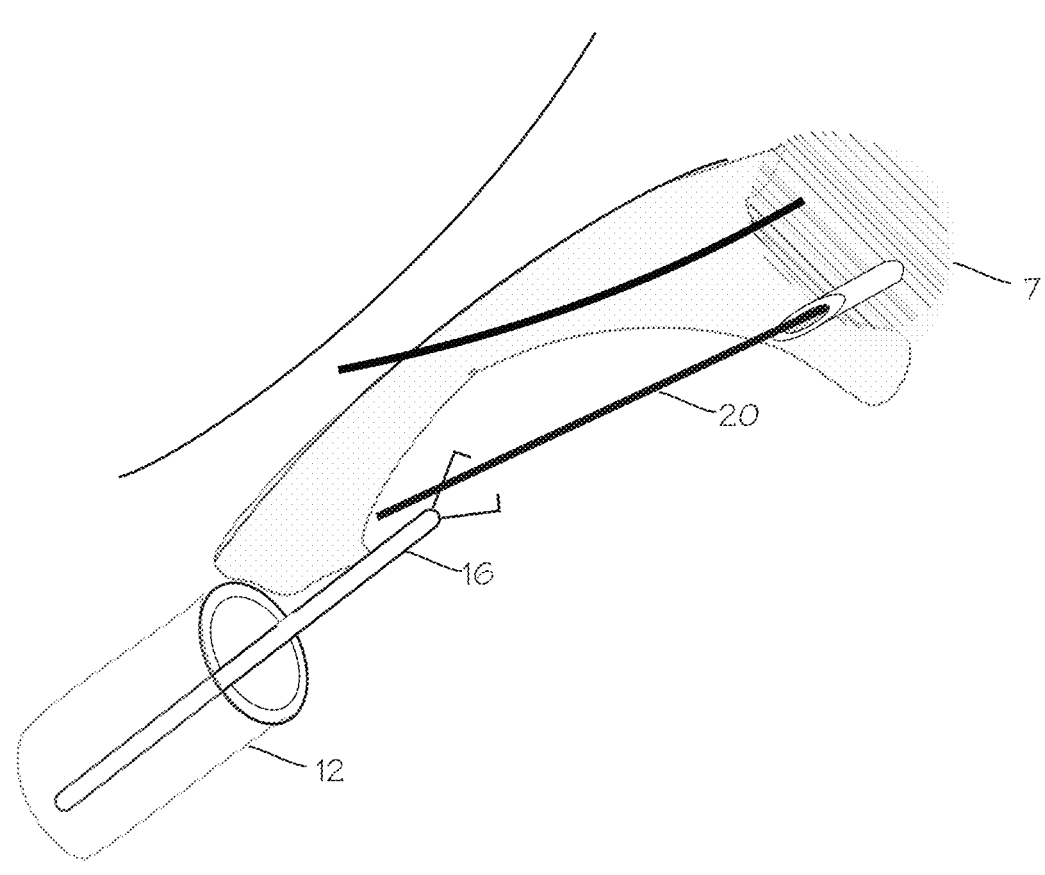
FIG. 5 illustrates The traction sutures are grasped and pulled through the anterior portal through the cannula in the rotator interval.

FIG. 5 illustrates the construct being pulled to the articular side tear via the traction sutures. The construct is advanced toward the articular side tear without completion of the tear from the bursal side. The partial tear is maintained as a partial tear and not completed into a total tear. The regenerative patch is applied directly to the tear on the articular side for optimal healing.

Figures 6, 7:
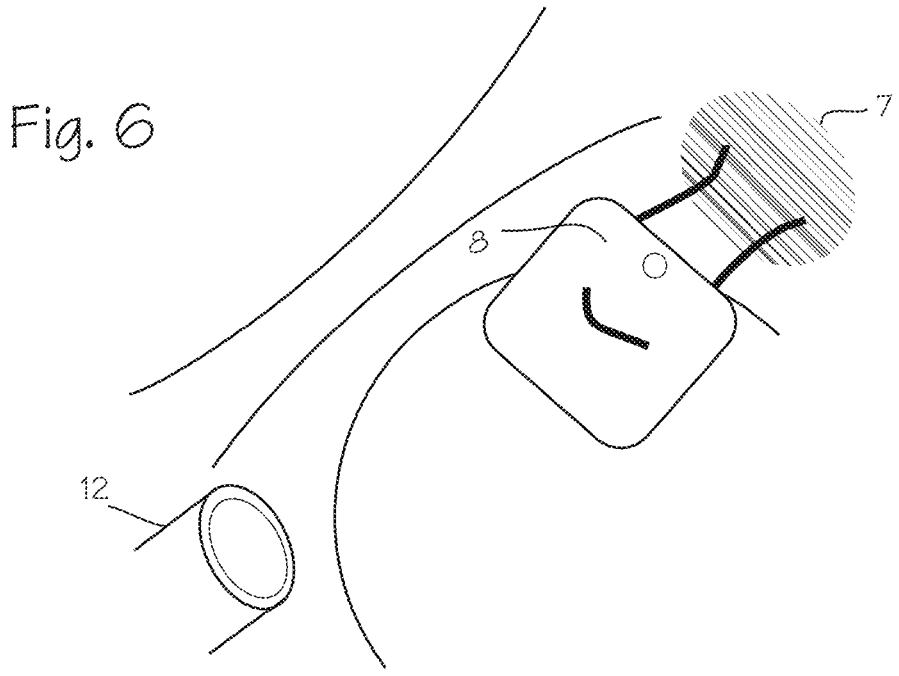
FIG. 6 illustrates the construct advanced through the glenohumeral joint space and advanced toward the articular sided tear.
FIG. 7 illustrates the construct placed over the articular sided tear.

FIG. 6 illustrates the construct 8 advanced through the glenohumeral joint space and advanced toward the articular sided tear 7. FIG. 7 illustrates the construct 8 placed over the articular sided tear. FIG. 8 illustrates the knotted sutures on the bursal side after placement of the construct against the articular side tear.

The rolled construct emerges in a rolled position from the anterior cannula. FIG. 6 illustrates the construct once it is completely out of the anterior cannula, in the glenohumeral joint space as is advances toward the articular sided tear. FIG. 7 illustrates that the construct is attached to a suture string long enough to follow the construct to the tendon repair site at a first end and also trail to the top of the tendon surface at the second end. This provides access and placement of the repair patch to the articular side through the tendon. FIG. 7 illustrates once the patch is delivered to the articular tear site, the sutures are passed through the rotator cuff to lay the patch against the tear. FIG. 8 illustrates the sutures are then pulled to the tear and tensioned against the compressed construct to secure the construct against the articular side tear of the rotator cuff. To tension the construct, the suture is pulled from the first end to oppose the construct to the tendon tear. The second suture end that is on the bursal side is also tightened or pulled to the bone to ensure secure placement of the construct. FIG. 8 illustrates the sutures tied on the bursal side of the tendon. The sutures can optionally be secured to a pledget, sponge, pack or plate or anything absorbent to help manage fluids and hold a bioactive substance.

The construct may alternatively be inserted through the roller cone in the anterior portal and the suture tails retrieved with a small diameter penetrating suture grasper through the rotator cuff tendon, without the use of traction sutures, and the sutures tied on to the bursal side of the rotator cuff to compress the construct against the articular sided partial tear.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A method of repairing a torn rotator cuff tendon having an articular or a bottom side and a bursal or top side of a patient's shoulder joint comprising the steps of:

establishing an arthroscopic or anterior portal through a rotator cuff interval of a shoulder that can access a glenohumeral space of the shoulder;

establishing a lateral portal within the shoulder, the lateral portal positioned opposite the articular side of the torn rotator cuff tendon;

inserting a delivery device having a proximal and distal end, through the arthroscopic portal;

inserting a spinal needle through the lateral portal and introducing at least two traction sutures through the rotator cuff interval and then using a grasper to pull the two traction sutures out through the arthroscopic portal and then removing the spinal needle;

providing a biological construct that has at least two suture tails on an end of the biological construct and tying the suture tails to the traction sutures;

advancing the biological construct via an inserter through the delivery device, the construct being in a first unrolled position at the proximal end of the delivery device, then inserted through the delivery device in a second rolled position, and then advanced through the delivery device into a third unrolled position into the glenohumeral space of the shoulder;

positioning the biological construct onto the articular or bottom side of the torn rotator cuff tendon and tightening the traction sutures on the articular or bottom side;

withdrawing the construct suture tails out of the lateral portal and clipping off the traction sutures, tying the suture tails on the bursal side of the torn tendon with the construct compressed to the articular side of the torn tendon with the suture tails tied off on the bursal or top side of the torn tendon; and maintaining the biological construct in place to heal the tendon.

2. The method of claim 1 further comprising the step of:

establishing a viewing portal through a posterior portal of the shoulder and distending the joint through the viewing portal.

3. The method of claim 1 further comprising the step of:

attaching a pledget or a second biological construct to the suture tails for connection on the bursal side of the torn rotator cuff tendon for additional support.

4. A method of repairing a torn rotator cuff tendon of a patient's shoulder joint comprising the steps:

establishing an arthroscopic or anterior portal through a rotator cuff interval of a shoulder that can access a glenohumeral space of the shoulder;

establishing a lateral portal within the shoulder, the lateral portal positioned opposite an articular or a bottom side of the torn rotator cuff tendon;

inserting a delivery device having a proximal and distal end, through the arthroscopic portal;

inserting a cannula through the lateral portal and introducing at least two traction sutures through the rotator cuff interval and then removing the cannula;

providing a biological construct that has retention means on an articular or a bottom side of the construct and securing the retention means to the traction sutures;

advancing the biological construct through the delivery device, the construct being in a first unrolled position at the proximal end of the delivery device, then inserted through the delivery device in a second rolled position, and then advanced through the delivery device into a third unrolled position into the glenohumeral space of the shoulder;

positioning the biological construct onto the articular or bottom side of the torn rotator cuff tendon and tightening the traction sutures via tensioning means on the articular or bottom side; and maintaining the biological construct in place to heal the tendon.

5. The method of claim 4 further comprising the step of:

establishing a viewing portal through a posterior portal of the shoulder and distending the joint through the viewing portal.

6. The method of claim 4 further comprising the step of:

attaching a pledget or a second biological construct to the retention means for connection on the bursal side of the torn rotator cuff tendon for additional support.

* * * * *